United States Patent [19]
Bandman et al.

[11] Patent Number: 5,919,685
[45] Date of Patent: Jul. 6, 1999

[54] HUMAN AFLATOXIN B1 ALDEHYDE REDUCTASE

[75] Inventors: Olga Bandman, Mountain View; Purvi Shah, Sunnyvale; Karl J. Guegler, Menlo Park; Neil C. Corley, Mountain View, all of Calif.

[73] Assignee: Incyte Pharmaceuticals, Inc., Palo Alto, Calif.

[21] Appl. No.: 08/907,674

[22] Filed: Aug. 8, 1997

[51] Int. Cl.$^6$ .............................. C12N 9/04; C12N 15/09; C12N 15/70; C12N 15/53

[52] U.S. Cl. ................. 435/190; 435/252.3; 435/252.33; 435/325; 435/320.1; 435/419; 435/254.11; 435/254.3; 536/23.2; 536/24.31

[58] Field of Search ................................. 435/190, 252.3, 435/252.33, 325, 320.1, 419, 254.11, 254.3; 536/23.2, 24.31

[56] References Cited

PUBLICATIONS

Hayes, J.D., et al., "Resistance to Aflatoxin B1 Is Associated with the Expression of a Novel Aldo–Keto Reductase Which Has Catalytic Activity Towards a Cytotoxic Aldehyde— containing Metabolite of the Toxin", *Cancer Research*, 53:3887–3894 (1993).

Judah, D.J., et al., "A novel aldehyde reductase with activity towards a metabolite of aflatoxin B1 is expressed in rat liver during carcinogenesis and following the administration of an anti–oxidant", *Biochem J*, 292:13–18 (1993).

Ellis, E.M., et al., "An ethoxyquin–inducible aldehyde reductase from rat liver that metabolizes aflatoxin $B_1$ defines a subfamily of aldo–keto reductases", *Proc. Natl Acad Sci, USA*, 90:10350–10354 (1993). (GI 433610) (GI 433611).

McGlynn, K.A., et al., "Susceptibility to hepatocellular carcinoma is associated with genetic variation in the enzymatic detoxification of aflatoxin $B_1$", *Proc. Natl Acad Sci, USA*, 92:2384–2387 (1995).

Aquilar, F., et al., "Aflatoxin $B_1$ induces the transversion of G→T in codon 249 of the p53 tumor suppressor gene in human hepatocytes", *Proc Natl Acad Sci USA*, 90:8586–8590 (1993).

Ellis, E.M., (GI 433611) GenBank Sequence Database (Accession X74673), National Center for Biotechnology Information: National Library of Medicine, Bethesda, Maryland 20849 No Year Provided.

Ellis, E.M., (GI 433610) GenBank Sequence Database (Accession X74673), National Center for Biotechnology Information: National Library of Medicine, Bethesda, Maryland 20849 No Year Provided.

Ellis et al. "An ethoxyquin–inductible aldehyde reductase from rat liver that metabolizes aflatoxin B1 defines a subfamily of aldo–keto reductases" Proc. Natl. Acad. Sci. U.S.A. 90 (21), 10350–10354 (1993), Nov. 1, 1993.

Genbank Accession X74673 "R.norvegicus AFAR mRNA for aflatoxin B1 aldehyde reductase." Submitted by E.M. Ellis, May 9, 1996.

Genbank Accession Q60770 "Human brain Expressed Sequence Tag EST00883" Submitted by MD Adams et al, Mar. 16, 1994.

Wells et al. "Additivity of mutational effects in proteins" Biochemistry 29 (37), 8509–8517, Sep. 18, 1990.

*Primary Examiner*—Keith D. Hendricks
*Assistant Examiner*—Bradley S. Mayhew
*Attorney, Agent, or Firm*—Leanne C. Price, Esq.; Lucy J. Billings, Esq.; Incyte Pharmaceuticals, Inc.

[57] ABSTRACT

The invention provides a human aflatoxin B1 aldehyde reductase (AFB1-hAR) and polynucleotides which identify and encode AFB1-hAR. The invention also provides expression vectors, host cells, agonists, antibodies and antagonists. The invention also provides methods for treating disorders associated with expression of AFB1-hAR.

8 Claims, 8 Drawing Sheets

```
5' CGA CCG CTG CGC GCG GCT CCT GGG CTG TCA CAG TCT CCC GTT GCC GCC GTC ATG
                  9              18              27              36              45              54
                                                                                                   M

TCC CGG CAG CTG TCG GCC CGG GCC CCA GCC ACG GTG CTG GGC GCC ATG GAG ATG
    S   R   Q   L   S   A   R   A   P   A   T   V   L   G   A   M   E   M
                 63              72              81              90              99             108

GGG CGC CGC ATG GAC ACG GCG CCC AGC GCC GCA GTC ACG CGC GCC TTC CTG GAG
    G   R   R   M   D   T   A   P   S   A   A   V   T   R   A   F   L   E
                117             126             135             144             153             162

CGC GGC CAC ACC GAG ATA GAC ACG GCC TTC GTG TAC AGC GAG GGC CAG TCC GAG
    R   G   H   T   E   I   D   T   A   F   V   Y   S   E   G   Q   S   E
                171             180             189             198             207             216

ACC ATC CTT GGC GGC CTG GGG CTC CGG CTG GGT GGC GGC GAC TGC AGA GTG AAA
    T   I   L   G   G   L   G   L   R   L   G   G   G   D   C   R   V   K
                225             234             243             252             261             270

ATT GCC ACC AAG GCC AAC CCT TGG GAT GGA AAA TCA CTA AAG CCT GAC AGT GTC
    I   A   T   K   A   N   P   W   D   G   K   S   L   K   P   D   S   V
                279             288             297             306             315             324

CGG TCC CAG CTG GAG ACG TCA TTG AAG AGG CTG CAG TGT CCC CAA GTG GAC CTC
    R   S   Q   L   E   T   S   L   K   R   L   Q   C   P   Q   V   D   L
                333             342             351             360             369             378
```

FIG. 1A

```
       387           396           405           414           423           432
TTC TAC CTA CAC ACA CCT GAC CAC GGC ACC CCG GTG GAA GAG ACG CTG CAT GCC
 F   Y   L   H   T   P   D   H   G   T   P   V   E   E   T   L   H   A
       441           450           459           468           477           486
TGC CAG CGG CTG CAC CAG GAG GGC AAG TTC GTG GAG CTT GGC CTC TCC AAC TAT
 C   Q   R   L   H   Q   E   G   K   F   V   E   L   G   L   S   N   Y
       495           504           513           522           531           540
GCT AGC TGG GAA GTG GCC GAG ATC ACC TGT TGC AAG AGC AAT GGC TGG ATC
 A   S   W   E   V   A   E   I   T   C   C   K   S   N   G   W   I
       549           558           567           576           585           594
CTG ACT GTG TAC CAG GGC ATG AAT GCC ATC ACC CGG CAG GTG GAA ACG
 L   T   V   Y   Q   G   M   N   A   I   T   R   Q   V   E   T
       603           612           621           630           639           648
GAG CTC TTC CCC TGC AGG CAC TTT GGA CTG AGG TTC TAT GCC TAC AAC CCT
 E   L   F   P   C   R   H   F   G   L   R   F   Y   A   Y   N   P
       657           666           675           684           693           702
CTG GCT GGG GGC CTG ACC GGC CTG ACC AAG TAC AAG TAT GAG GAC AAG GAT GGG AAA
 L   A   G   G   L   T   G   L   T   K   Y   K   Y   E   D   K   D   G   K
       711           720           729           738           747           756
CAG CCT GTG GGC CGC TTC TTT GGG AAT ACC TGG GCA GAG ATG TAC AGG AAT CGC
 Q   P   V   G   R   F   F   G   N   T   W   A   E   M   Y   R   N   R
```

FIG. 1B

```
      765                774           783           792           801           810
TAC TGG AAG GAG CAC TTC GAG GGC ATT GCC CTG GTG GAG AAG GCC CTG CAG
 Y   W   K   E   H   F   E   G   I   A   L   V   E   K   A   L   Q
      819                828           837           846           855           864
GCC GCG TAT GGC TGC AGC GCC CCC AGT GTG ACC TCG GCT GCC CTC CGG TGG ATG
 A   A   Y   G   C   S   A   P   S   V   T   S   A   A   L   R   W   M
      873                882           891           900           909           918
TAC CAC CAC TCA CAG CTG CAG GGT GCC CAC GGG GAC GCG GTC ATC CTG GGC ATG
 Y   H   H   S   Q   L   Q   G   A   H   G   D   A   V   I   L   G   M
      927                936           945           954           963           972
TCC AGC CTG GAG CAG CTG GAG CAG AAC TTG GCA GCA ACA GAG GAA GGG CCC CTG
 S   S   L   E   Q   L   E   Q   N   L   A   A   T   E   E   G   P   L
      981                990          999          1008          1017          1026
GAG CCG GCT GTC GTG GAT GCC TTT AAT CAA GCC TGG CAT TTG GTT GCT CAC GAA
 E   P   A   V   V   D   A   F   N   Q   A   W   H   L   V   A   H   E
     1035               1044          1053          1062          1071          1080
TGT CCC AAC TAC TTC CGC TAG GCC CAT CAT GGC TCA GGC TGC CCA AGG CTT TTC
 C   P   N   Y   F   R
     1089               1098          1107          1116          1125          1134
TGT CAC CTC TTT TGT TCT CTC ACA CTG ACC AGT CTT GGC CTT AAG CTG ACT TAG
```

FIG. 1C

```
                                                1143            1152            1161            1170            1179            1188
                                                AAG GGT TTT TCT GAA TTG TCT AGA TCC ATG CAT TAT TTT TCT AGC TTC CTG CCT 1197            1206            1215            1224            1233            1242
                                                TGC TCC CTA TTC ACT TTA CAC TGT GAA AGG TGG GGG GTG AGT CCC ACT TGA GCG 1251            1260            1269            1278            1287            1296
                                                CTT CCT GTT GAA TAA AGC AGG CAC TTG ACC TGG CTG TAG CCT AGG TCT TGA GTG 1305            1314            1323            1332            1341            1350
                                                AAC CCC AAA AAA AAA AAA AAA GGC GGC GCT ACC GCG GTG AGC TCC AGC TGT GTC 1359            1368
                                                CCT TAG TAG GTA ATT CGC CTG CA 3'
```

FIG. 1D

| | | |
|---|---|---|
| 1 | M S R Q L S R A R P A T V L G A M E M G | 1596452 |
| 1 | M - - - - S Q A R P A T V L G A M E M G | GI 433611 |
| 21 | R R M D A P T S A A V T R A F L E R G H | 1596452 |
| 17 | R R M D V T S S S A S V R A F L Q R G H | GI 433611 |
| 41 | T E I D T A F V Y S E G Q S E T I L G G | 1596452 |
| 37 | T E I D T A F V Y A N G Q S E T I L G D | GI 433611 |
| 61 | L G L R L G G G D C R V K I A T K A N P | 1596452 |
| 57 | L G L G L G R S G C K V K I A T K A A P | GI 433611 |
| 81 | W D G K S L K P D S V R S Q L E T S L K | 1596452 |
| 77 | M F G K T L K P A D V R F Q L E T S L K | GI 433611 |
| 101 | R L Q C P Q V D L F Y L H T P D H G T P | 1596452 |
| 97 | R L Q C P R V D L F Y L H F P D H G T P | GI 433611 |
| 121 | V E E T L H A C Q R L H Q E G K F V E L | 1596452 |
| 117 | I E E T L Q A C H H V H Q E G K F V E L | GI 433611 |
| 141 | G L S N Y A S W E V A E I C T L C K S N | 1596452 |
| 137 | G L S N Y V S W E V A E I C T L C K K N | GI 433611 |
| 161 | G W I L P T V Y Q G M Y N A I T R Q V E | 1596452 |
| 157 | G W I M P T V Y Q G M Y N A I T R Q V E | GI 433611 |
| 181 | T E L F P C L R H F G L R F Y A Y N P L | 1596452 |
| 177 | T E L F P C L R H F G L R F Y A F N P L | GI 433611 |
| 201 | A G G L L T G K Y K Y E D K D G K Q P V | 1596452 |
| 197 | A G G L L T G R Y K Y Q D K D G K N P E | GI 433611 |

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 331 amino acids
       (B) TYPE: amino acid
       (C) STRANDEDNESS: single
       (D) TOPOLOGY: linear (vii) IMMEDIATE SOURCE:
       (A) LIBRARY: BRAINOT14
       (B) CLONE: 1596452

(xi) SEQUENCE DESCRIPTION: SEQ ID NO:1:

```
Met Ser Arg Gln Leu Ser Arg Ala Arg Pro Ala Thr Val Leu Gly Ala
1               5                   10                  15

Met Glu Met Gly Arg Arg Met Asp Ala Pro Thr Ser Ala Ala Val Thr
            20                  25                  30

Arg Ala Phe Leu Glu Arg Gly His Thr Glu Ile Asp Thr Ala Phe Val
        35                  40                  45

Tyr Ser Glu Gly Gln Ser Glu Thr Ile Leu Gly Gly Leu Gly Leu Arg
    50                  55                  60

Leu Gly Gly Gly Asp Cys Arg Val Lys Ile Ala Thr Lys Ala Asn Pro
65                  70                  75                  80

Trp Asp Gly Lys Ser Leu Lys Pro Asp Ser Val Arg Ser Gln Leu Glu
                85                  90                  95

Thr Ser Leu Lys Arg Leu Gln Cys Pro Gln Val Asp Leu Phe Tyr Leu
            100                 105                 110

His Thr Pro Asp His Gly Thr Pro Val Glu Thr Leu His Ala Cys
        115                 120                 125

Gln Arg Leu His Gln Glu Gly Lys Phe Val Glu Leu Gly Leu Ser Asn
    130                 135                 140

Tyr Ala Ser Trp Glu Val Ala Glu Ile Cys Thr Leu Cys Lys Ser Asn
145                 150                 155                 160

Gly Trp Ile Leu Pro Thr Val Tyr Gln Gly Met Tyr Asn Ala Ile Thr
                165                 170                 175

Arg Gln Val Glu Thr Glu Leu Phe Pro Cys Leu Arg His Phe Gly Leu
            180                 185                 190

Arg Phe Tyr Ala Tyr Asn Pro Leu Ala Gly Leu Leu Thr Gly Lys
    195                 200                 205

Tyr Lys Tyr Glu Asp Lys Asp Gly Lys Gln Pro Val Gly Arg Phe Phe
    210                 215                 220

Gly Asn Thr Trp Ala Glu Met Tyr Arg Asn Arg Tyr Trp Lys Glu His
225                 230                 235                 240

His Phe Glu Gly Ile Ala Leu Val Glu Lys Ala Leu Gln Ala Ala Tyr
                245                 250                 255

Gly Ala Ser Ala Pro Ser Val Thr Ser Ala Ala Leu Arg Trp Met Tyr
            260                 265                 270

His His Ser Gln Leu Gln Gly Ala His Gly Asp Ala Val Ile Leu Gly
        275                 280                 285

Met Ser Ser Leu Glu Gln Leu Glu Gln Asn Leu Ala Ala Thr Glu Glu
    290                 295                 300

Gly Pro Leu Glu Pro Ala Val Val Asp Ala Phe Asn Gln Ala Trp His
```

|     |     |     |     |     |
| --- | --- | --- | --- | --- | 
| 305 |  | 310 | 315 | 320 |

Leu Val Ala His Glu Cys Pro Asn Tyr Phe Arg
                325               330

(2) INFORMATION FOR SEQ ID NO:2:

(i) SEQUENCE CHARACTERISTICS:
        (A) LENGTH: 1373 base pairs
        (B) TYPE: nucleic acid
        (C) STRANDEDNESS: single
        (D) TOPOLOGY: linear (vii) IMMEDIATE SOURCE:
        (A) LIBRARY: BRAINOT14
        (B) CLONE: 1596452

(xi) SEQUENCE DESCRIPTION: SEQ ID NO:2:

```
CGACCGCTGC GCGCGGCTCC TGGGCTGTCA CAGTCTCCCG TTGCCGCCGT CATGTCCCGG     60

CAGCTGTCGC GGGCCCGGCC AGCCACGGTG CTGGGCGCCA TGGAGATGGG GCGCCGCATG    120

GACGCGCCCA CCAGCGCCGC AGTCACGCGC GCCTTCCTGG AGCGCGGCCA CACCGAGATA    180

GACACGGCCT TCGTGTACAG CGAGGGCCAG TCCGAGACCA TCCTTGGCGG CCTGGGGCTC    240

CGGCTGGGCG GTGGCGACTG CAGAGTGAAA ATTGCCACCA AGGCCAACCC TTGGGATGGA    300

AAATCACTAA AGCCTGACAG TGTCCGGTCC CAGCTGGAGA CGTCATTGAA GAGGCTGCAG    360

TGTCCCCAAG TGGACCTCTT CTACCTACAC ACACCTGACC ACGGCACCCC GGTGGAAGAG    420

ACGCTGCATG CCTGCCAGCG GCTGCACCAG GAGGGCAAGT TCGTGGAGCT TGGCCTCTCC    480

AACTATGCTA GCTGGGAAGT GGCCGAGATC TGTACCCTCT GCAAGAGCAA TGGCTGGATC    540

CTGCCCACTG TGTACCAGGG CATGTACAAT GCCATCACCC GGCAGGTGGA AACGGAGCTC    600

TTCCCCTGCC TCAGGCACTT TGGACTGAGG TTCTATGCCT ACAACCCTCT GGCTGGGGGC    660

CTGCTGACCG GCAAGTACAA GTATGAGGAC AAGGATGGGA ACAGCCTGT GGGCCGCTTC    720

TTTGGGAATA CCTGGGCAGA GATGTACAGG AATCGCTACT GGAAGGAGCA CCACTTCGAG    780

GGCATTGCCC TGGTGGAGAA GGCCCTGCAG GCCGCGTATG CGCCAGCGC CCCCAGTGTG    840

ACCTCGGCTG CCCTCCGGTG GATGTACCAC CACTCACAGC TGCAGGGTGC CCACGGGGAC    900

GCGGTCATCC TGGGCATGTC CAGCCTGGAG CAGCTGGAGC AGAACTTGGC AGCAACAGAG    960

GAAGGGCCCC TGGAGCCGGC TGTCGTGGAT GCCTTTAATC AAGCCTGGCA TTTGGTTGCT   1020

CACGAATGTC CCAACTACTT CCGCTAGGCC CATCATGGCT CAGGCTGCCC AAGGCTTTTC   1080

TGTCACCTCT TTTGTTCTCT CACACTGACC AGTCTTGGCC TTAAGCTGAC TTAGAAGGGT   1140

TTTTCTGAAT TGTCTAGATC CATGCATTAT TTTTCTAGCT TCCTGCCTTG CTCCCTATTC   1200

ACTTTACACT GTGAAAGGTG GGGGGTGAGT CCCACTTGAG CGCTTCCTGT TGAATAAAGC   1260

AGGCACTTGA CCTGGCTGTA GCCTAGGTCT TGAGTGAACC CCAAAAAAAA AAAAAAGGC   1320

GGCGCTACCG CGGTGAGCTC CAGCTGTGTC CCTTAGTAGG TAATTCGCCT GCA         1373
```

(2) INFORMATION FOR SEQ ID NO:3:

(i) SEQUENCE CHARACTERISTICS:
        (A) LENGTH: 327 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 433611

(xi) SEQUENCE DESCRIPTION: SEQ ID NO:3:

-continued

```
Met Ser Gln Ala Arg Pro Ala Thr Val Leu Gly Ala Met Glu Met Gly
 1           5                  10                  15

Arg Arg Met Asp Val Thr Ser Ser Ser Ala Ser Val Arg Ala Phe Leu
             20                  25                  30

Gln Arg Gly His Thr Glu Ile Asp Thr Ala Phe Val Tyr Ala Asn Gly
         35                  40                  45

Gln Ser Glu Thr Ile Leu Gly Asp Leu Gly Leu Gly Leu Gly Arg Ser
     50                  55                  60

Gly Cys Lys Val Lys Ile Ala Thr Lys Ala Ala Pro Met Phe Gly Lys
 65                  70                  75                  80

Thr Leu Lys Pro Ala Asp Val Arg Phe Gln Leu Glu Thr Ser Leu Lys
             85                  90                  95

Arg Leu Gln Cys Pro Arg Val Asp Leu Phe Tyr Leu His Phe Pro Asp
            100                 105                 110

His Gly Thr Pro Ile Glu Glu Thr Leu Gln Ala Cys His His Val His
            115                 120                 125

Gln Glu Gly Lys Phe Val Glu Leu Gly Leu Ser Asn Tyr Val Ser Trp
        130                 135                 140

Glu Val Ala Glu Ile Cys Thr Leu Cys Lys Lys Asn Gly Trp Ile Met
145                 150                 155                 160

Pro Thr Val Tyr Gln Gly Met Tyr Asn Ala Ile Thr Arg Gln Val Glu
                165                 170                 175

Thr Glu Leu Phe Pro Cys Leu Arg His Phe Gly Leu Arg Phe Tyr Ala
            180                 185                 190

Phe Asn Pro Leu Ala Gly Gly Leu Leu Thr Gly Arg Tyr Lys Tyr Gln
        195                 200                 205

Asp Lys Asp Gly Lys Asn Pro Glu Ser Arg Phe Phe Gly Asn Pro Phe
210                 215                 220

Ser Gln Leu Tyr Met Asp Arg Tyr Trp Lys Glu Glu His Phe Asn Gly
225                 230                 235                 240

Ile Ala Leu Val Glu Lys Ala Leu Lys Thr Thr Tyr Gly Pro Thr Ala
                245                 250                 255

Pro Ser Met Ile Ser Ala Ala Val Arg Trp Met Tyr His His Ser Gln
                260                 265                 270

Leu Lys Gly Thr Gln Gly Asp Ala Val Ile Leu Gly Met Ser Ser Leu
        275                 280                 285

Glu Gln Leu Glu Gln Asn Leu Ala Leu Val Glu Glu Gly Pro Leu Glu
        290                 295                 300

Pro Ala Val Val Asp Ala Phe Asp Gln Ala Trp Asn Leu Val Ala His
305                 310                 315                 320

Glu Cys Pro Asn Tyr Phe Arg
                325
```

HUMAN AFLATOXIN B1 ALDEHYDE REDUCTASE

FIELD OF THE INVENTION

This invention relates to nucleic acid and amino acid sequences of a human aflatoxin B1 aldehyde reductase and to the use of these sequences in the diagnosis, prevention, and treatment of gastrointestinal and neoplastic disorders.

BACKGROUND OF THE INVENTION

Aflatoxin B1 (AFB1) is a potent environmental carcinogen produced by the common molds *Aspergillus favus, A. parasiticus*, and *A. nominus*. Human exposure results principally from the ingestion of stored foodstuffs contaminated with these molds. Carcinogenicity is associated with the conversion of AFB1 to its 8,9-oxide by the hepatic cytochrome P450-dependent monooxygenase system. Ingestion of food contaminated with fungal aflatoxins is believed to contribute to the high incidence of hepatoma and chronic liver disease in subtropical regions.

Hayes, J. D. et al. (1993; Cancer Res. 53:3887–3894) reported that expression of an aldehyde reductase (AR) is induced in the liver of rats fed on an ethoxyquin-containing diet. Ethoxyquin activates transcription of several liver detoxification enzymes. Induction of expression of the aldehyde reductase is correlated with resistance to AFB1-induced carcinogenesis. The enzyme, AFB1-AR, catalyzes the formation of a dialcohol from the cytotoxic dialdehyde form of AFB1-8,9-dihydrodiol (Judah, D. J. et al. (1993) Biochem J. 292:13–18). Ellis, E. M. et al. (1993; Proc. Natl. Acad. Sci. USA 90:10350–10354) isolated cDNA which encodes AFB1-AR and observed that the AFB1-AR protein sequence defines a previously unrecognized subclass of the aldehyde reductase superfamily. AFB1-AR is 327 amino acids in length and contains a putative active site histidine at position 109.

Primary hepatocellular carcinoma (HCC) occurs with high frequency in eastern Asia and sub-Saharan Africa. In these areas of the world, chronic hepatitis B virus (HBV) infection is the best described risk factor for HCC; however, only 20–25% of HBV carriers develop HCC (McGlynn, K. A. et al. (1995) Proc. Natl. Acad. Sci. USA 92:2384–2387). In certain areas of the HCC endemic regions, an unusual mutational hot spot has been reported in the p53 tumor suppressor gene. This mutation, at codon 249 in exon 7, is an AGG-to-AGT transversion (arginine to serine). The geographic distribution of these mutations and the similarity of these mutations to the transversions produced in vitro by AFB1 suggest that exposure to AFB1 causes the p53 mutation. Demonstration of the preferential mutability of p53 codon 249 by rat liver microsome-activated AFB1 in HepG2 cells supports this hypothesis (Aguilar, F. et al. (1993) Proc. Natl. Acad. Sci. USA 90:8586–8590).

AFB1 is metabolized and detoxified in the liver via detoxification pathways. McGlynn et al. (supra) proposed that genetic variation in AFB1 detoxification genes may define susceptibility to the effects of AFB. To test their hypothesis, genetic variation in two AFB1 detoxification genes, epoxide hydrolase (EPHX) and glutathione S-transferase M1 (GSTM1), was compared with the presence of serum AFB1-albumin adducts, the presence of hepatocellular carcinoma (HCC), and with p53 codon 249 mutations. Mutant alleles at both loci were significantly over-represented in individuals with serum AFB1-albumin adducts in a cross-sectional study. In a case-control study mutant alleles of EPHX were significantly overrepresented in persons with HCC. The relationship of EPHX to HCC varied by hepatitis B surface antigen status and indicated that a synergistic effect may exist. p53 codon 249 mutations were observed only among HCC patients with one or both high-risk genotypes. These results indicate that individuals with mutant genotypes at EPHX and GSTM1may be at greater risk of developing AFB1 adducts, p53 mutations, and HCC when exposed to AFB1. Hepatitis B carriers with the high-risk genotypes may bear even greater risk than carriers with low-risk genotypes. These findings by McGlynn et al. (supra) support the existence of genetic susceptibility in humans to the environmental carcinogen AFB1 and indicate that there is a synergistic increase in risk of HCC with the combination of hepatitis B virus infection and susceptible genotype.

The discovery of a new human aflatoxin B1 aldehyde reductase and the polynucleotides encoding it satisfies a need in the art by providing new compositions which are useful in the diagnosis, prevention and treatment of gastrointestinal and neoplastic disorders.

SUMMARY OF THE INVENTION

The invention features a substantially purified polypeptide, human aflatoxin B1 aldehyde reductase (AFB1-hAR), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding AFB1-hAR under conditions suitable for the expression of the polypeptide; and b) recovering the polypeptide from the host cell culture.

The invention also provides a pharmaceutical composition comprising a substantially purified AFB1-hAR having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a gastrointestinal disorder comprising administering to a subject in need of such treatment an effective amount of a pharmaceutical composition comprising purified AFB1-hAR.

The invention also provides a method for treating or preventing a neoplastic disorder comprising administering to a subject in need of such treatment an effective amount of a pharmaceutical composition comprising purified AFB1-hAR.

The invention also provides a method for detecting a polynucleotide which encodes AFB1-hAR in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding AFB1-hAR in the biological sample. In one aspect the nucleic acid material of the biological sample is amplified by the polymerase chain reaction prior to a hybridization.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of AFB1-hAR. The alignment was produced using MACD-NASIS PRO software (Hitachi Software Engineering Co. Ltd. San Bruno, Calif.).

FIGS. 2A and 2B show the amino acid sequence alignments between AFB1-hAR (1596452; SEQ ID NO:1) and AFB1-AR from rat liver (GI 433611; SEQ ID NO:3), produced using the multisequence alignment program of DNASTAR™ software (DNASTAR Inc. Madison Wis.).

DESCRIPTION OF THE INVENTION

Figure 3A:
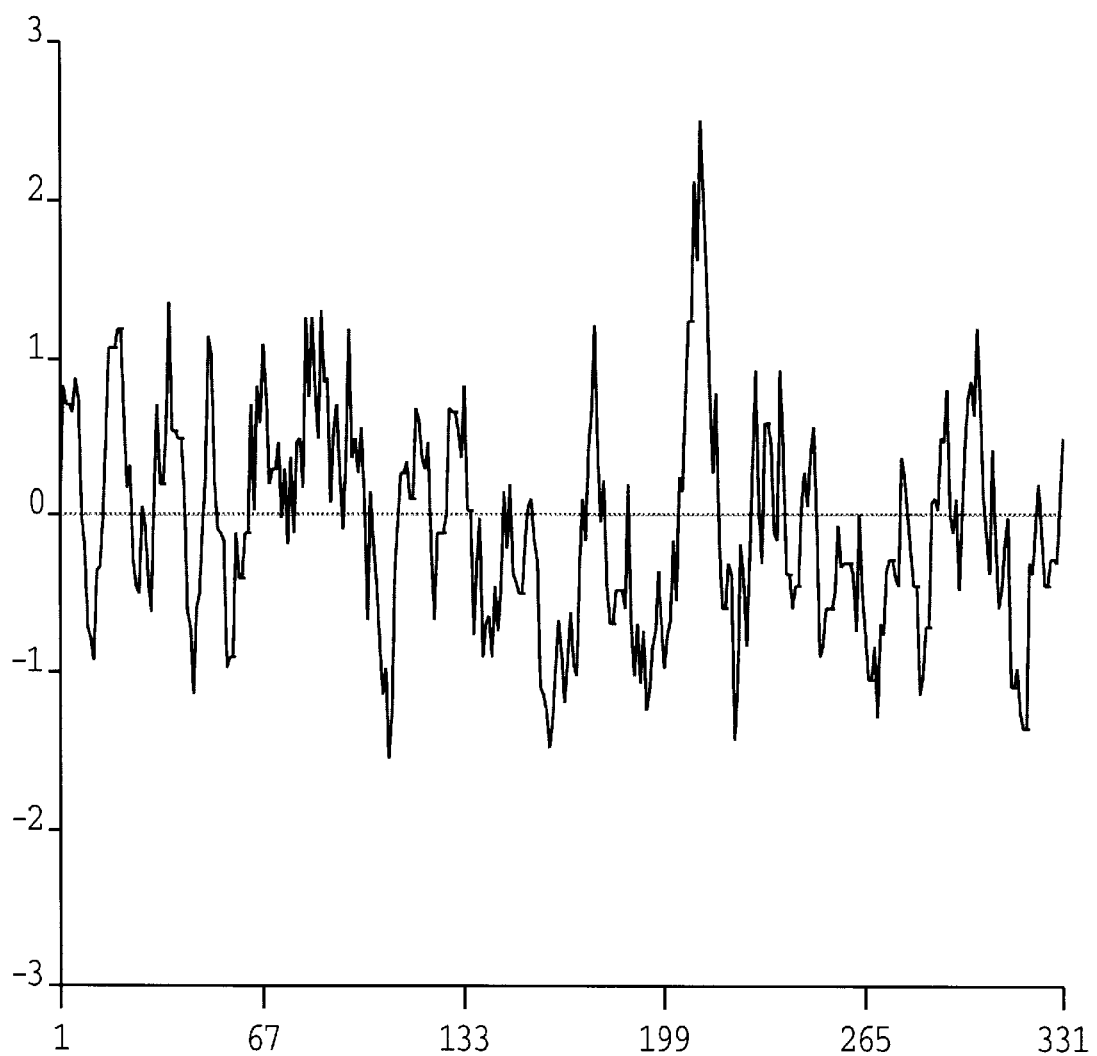
FIGS. 3A and 3B show the hydrophobicity plots for AFB1-hAR (SEQ ID NO:1) and rat liver AFB1-AR (SEQ ID NO:3), respectively; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

AFB1-hAR, as used herein, refers to the amino acid sequences of substantially purified AFB1-hAR obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to AFB1-hAR, increases or prolongs the duration of the effect of AFB1-hAR. Agonists may include proteins, nucleic acids, carbohydrates, or any other molecules which bind to and modulate the effect of AFB1-hAR.

An "allele" or "allelic sequence", as used herein, is an alternative form of the gene encoding AFB1-hAR. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding AFB1-hAR as used herein include those with deletions, insertions, or substitutions of different nucleotides resulting in a polynucleotide that encodes the same or a functionally equivalent AFB1-hAR. Included within this definition are polymorphisms which may or may not be readily detectable using a particular oligonucleotide probe of the polynucleotide encoding AFB1-hAR, and improper or unexpected hybridization to alleles, with a locus other than the normal chromosomal locus for the polynucleotide sequence encoding AFB1-hAR. The encoded protein may also be "altered" and contain deletions, insertions, or substitutions of amino acid residues which produce a silent change and result in a functionally equivalent AFB1-hAR. Deliberate amino acid substitutions may be made on the basis of similarity in polarity, charge, solubility, hydrophobicity, hydrophilicity, and/or the amphipathic nature of the residues as long as the biological or immunological activity of AFB1-hAR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of AFB1-hAR are preferably about 5 to about 15 amino acids in length and retain the biological activity or the immunological activity of AFB1-hAR. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to AFB1-hAR, decreases the amount or the duration of the effect of the biological or immunological activity of AFB1-hAR. Antagonists may include proteins, nucleic acids, carbohydrates, antibodies or any other molecules which decrease the effect of AFB1-hAR.

As used herein, the term "antibody" refers to intact molecules as well as fragments thereof, such as Fab, F(ab')$_2$, and Fv, which are capable of binding the epitopic determinant. Antibodies that bind AFB1-hAR polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic AFB1-hAR, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding AFB1-hAR (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NACl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR extention kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of MRNA encoding AFB1-hAR in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to AFB1-hAR or the encoded AFB1-hAR. Such modifications include, for example, replacement of hydrogen by an alkyl, acyl, or amino group. A nucleic acid derivative encodes a polypeptide which retains tile biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACS) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of AFB1-hAR. For example, modulation may cause an increase or a decrease in protein activity, binding characteristics, or any other biological, functional or immunological properties of AFB1-hAR.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length AFB1-hAR and fragments thereof.

The term "sample", as used herein, is used in its broadest sense. A biological sample suspected of containing nucleic acid encoding AFB1-hAR, or fragments thereof, or AFB1-hAR itself may comprise a bodily fluid, extract from a cell, chromosome, organelle, or membrane isolated from a cell, a cell, genomic DNA, RNA, or DNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of AFB1-hAR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human aflatoxin B1 aldehyde reductase (hereinafter referred to as "AFB1-hAR"), the polynucleotides encoding AFB1-hAR, and the use of these compositions for the diagnosis, prevention, or treatment of gastrointestinal and neoplastic disorders.

Nucleic acids encoding the AFB1-hAR of the present invention were first identified in Incyte Clone 1596452 from the astrocytoma-associated brain tissue cDNA library BRAINOT14 using a computer search for amino acid sequence alignments. A consensus sequence, SEQ ID NO:2, was derived from the following overlapping and/or extended nucleic acid sequences: Incyte Clones 887238 (PANCNOT05), 1623504 (BRAITUT13), 1630438 (COLNNOT19), 1594652 (BRAINOT14), 1312614 (BLADTUT02), and 2350042 (COLSUCT01).

Figure 3B:
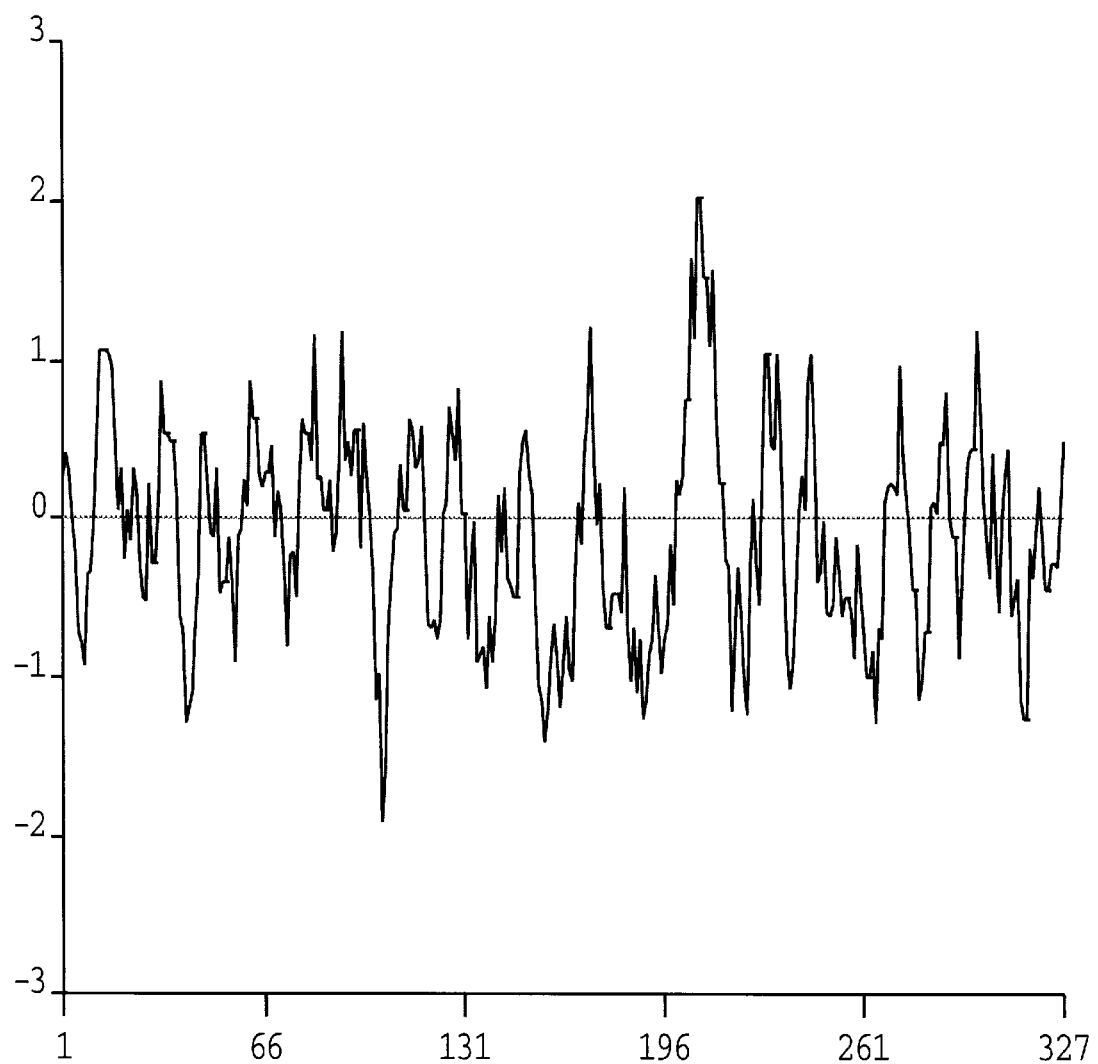

In one embodiment, the invention encompasses a polypeptide comprising the amino acid sequence of SEQ ID NO:1, as shown in FIGS. 1A, 1B, 1C, and 1D. AFB1-hAR is 331 amino acids in length and, as shown in FIGS. 2A and 2B, has chemical and structural homology with rat liver AFB1-AR (GI 433611; SEQ ID NO:3). In particular, AFB1-hAR and rat liver AFB1-AR share 80% amino acid sequence identity. The putative active site His109 of rat AFB1-AR aligns with His113 of AFB1-hAR. As illustrated by FIGS. 3A and 3B, AFB1-hAR and rat liver AFB-AR have similar hydrophobicity plots. Northern analysis shows the expression of AFB1-hAR in various libraries, including liver, colon, large intestine, small intestine, stomach, olfactory epithelium, brain, prostate, bladder, lung, heart, thyroid, parathyroid, ovary, kidney, and penis; epithelial cell lines from colon, nasal mucosa, and lung; fetal colon, placenta, lung, kidney, liver, and spleen. Of particular note is the expression of AFB1-hAR in disorders of the gastrointestinal system, including irritable bowel syndrome, ulcerative colitis, Crohn's disease, and cholecystitis; and in neoplastic disorders including tumors, polyps, and hyperplasia of the liver, colon, nasal cavity, prostate, bladder, thyroid, ovary, parathyroid, penis, and kidney. The similarity of AFB1-hAR to rat liver AFB1-AR and its association with disorders of the gastrointestinal tract and neoplastic disorders suggest that AFB1-hAR plays a role in the detoxification of AFB1 and related compounds. Furthermore, AFB1-hAR may be subject to transcriptional regulation by inducers such as ethoxyquin in a manner similar to rat AFB1-AR.

The invention also encompasses AFB1-hAR variants. A preferred AFB1-hAR variant is one having at least 80%, and more preferably at least 90%, amino acid sequence identity to the AFB1-hAR amino acid sequence (SEQ ID NO:1) and which retains at least one biological, immunological or other functional characteristic or activity of AFB1-hAR. A most preferred AFB1-hAR variant is one having at least 95% amino acid sequence identity to SEQ ID NO:1.

The invention also encompasses polynucleotides which encode AFB1-hAR. Accordingly, any nucleic acid sequence which encodes the amino acid sequence of AFB1-hAR can be used to produce recombinant molecules which express AFB1-hAR. In a particular embodiment, the invention encompasses the polynucleotide comprising the nucleic acid sequence of SEQ ID NO:2 as shown in FIGS. 1A, 1B, 1C, and 1D.

It will be appreciated by those skilled in the art that as a result of the degeneracy of the genetic code, a multitude of nucleotide sequences encoding AFB1-hAR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring AFB1-hAR, and all such variations are to be considered as being specifically disclosed.

Although nucleotide sequences which encode AFB1-hAR and its variants are preferably capable of hybridizing to the nucleotide sequence of the naturally occurring AFB1-hAR under appropriately selected conditions of stringency, it may be advantageous to produce nucleotide sequences encoding AFB1-hAR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding AFB1-hAR and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode AFB1-hAR and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding AFB1-hAR or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE DNA polymerase (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by Gibco/BRL (Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding AFB1-hAR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the a first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991, Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR software, Perkins Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode AFB1-hAR may be used in recombinant DNA molecules to direct expression of AFB1-bAR, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express AFB1-hAR.

As will be understood by those of skill in the art, it may be advantageous to produce AFB1-hAR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter AFB1-hAR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding AFB1-hAR may be ligated to a heterologous sequence to encode a fusion protein. For example, to screen peptide libraries for inhibitors of AFB1-hAR activity, it may be useful to encode a chimeric AFB1-hAR protein that can be recognized by a commercially available antibody. A fusion protein may also be engineered to contain a cleavage site located between the AFB1-hAR encoding sequence and the heterologous protein sequence, so that AFB1-hAR may be cleaved and purified away from the heterologous moiety.

In another embodiment, sequences encoding AFB1-hAR may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 7:225–232). Alternatively, the protein itself may be produced using chemical methods to synthesize the amino acid sequence of AFB1-hAR, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) Proteins, Structures and Molecular Principles, W H Freeman and Co., New York, N.Y.). The composition of the synthetic peptides may be confirmed by amino acid analysis or sequencing (e.g., the Edman degradation procedure; Creighton, supra). Additionally, the amino acid sequence of AFB1-hAR, or any part thereof, may be altered during direct synthesis and/or combined using chemical methods with sequences from other proteins, or any part thereof, to produce a variant polypeptide.

In order to express a biologically active AFB1-hAR, the nucleotide sequences encoding AFB1-hAR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding AFB1-hAR and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express be sequences encoding AFB1-hAR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CAMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding AFB1-hAR, vectors based on SV40 or EBV may be used with an appropriate selectable marker.

In bacterial systems, a number of expression vectors may be selected depending upon the use intended for AFB1-hAR. For example, when large quantities of AFB1-hAR are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding AFB1-hAR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding AFB1-hAR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Corazzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express AFB1-hAR. For example, in one such system, *Autographa californica* nuclear polyhedrosis virus (AcNPV) is used as a vector to express foreign genes in *Spodolptera frugiperda* cells or in Trichoplusia larvae. The sequences encoding AFB1-hAR may be cloned into a non-essential region of the virus, such as the polyhedrin gene, and placed under control of the polyhedrin promoter. Successful insertion of AFB1-hAR will render the polyhedrin gene inactive and produce recombinant virus lacking coat protein. The recombinant viruses may then be used to infect, for example, *S. frugiperda* cells or Trichoplusia larvae in which AFB1-hAR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding AFB1-hAR may be ligated into an adenovirus transcription/translation complex consisting of the late promoter and tripartite leader sequence. Insertion in a non-essential E1 or E3 region of the viral genome may be used to obtain a viable virus which is capable of expressing AFB1-hAR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding AFB1-hAR. Such signals include the ATG initiation codon and adjacent sequences. In cases where sequences encoding AFB1-hAR, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express AFB1-bAR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70), npt, which confers resistance to the aminoglycosides neomycin and G-418 (Colbere-Garapin, F. et al (1981) J. Mol. Biol. 150:1–14) and als or pat, which confer resistance to chlorsulfaron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1 995) Methods Mol. Biol. 55:121–131).

Although the presence/absence of marker gene expression suggests that the gene of interest is also present, its presence and expression may need to be confirmed. For example, if the sequence encoding AFB1-hAR is inserted within a marker gene sequence, transformed cells containing sequences encoding AFB1-hAR can be identified by the absence of marker gene function. Alternatively, a marker gene can be placed in tandem with a sequence encoding AFB1-hAR under the control of a single promoter. Expression of the marker gene in response to induction or selection usually indicates expression of the tandem gene as well.

Alternatively, host cells which contain the nucleic acid sequence encoding AFB1-hAR and express AFB1-hAR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding AFB1-hAR can be detected by DNA-DNA or DNA-RNA hybridization or amplification using probes or fragments or fragments of polynucleotides encoding AFB1-hAR. Nucleic acid amplification based assays involve the use of oligonucleotides or oligomers based on the sequences encoding AFB1-hAR to detect transformants containing DNA or RNA encoding AFB1-hAR.

A variety of protocols for detecting and measuring the expression of AFB1-hAR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on AFB1-hAR is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding AFB1-hAR include oligolabeling, nick translation, end-labeling or PCR amplification using a labeled nucleotide. Alternatively, the sequences encoding AFB1-hAR, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharinacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding AFB1-hAR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode AFB1-hAR may be designed to contain signal sequences which direct secretion of AFB1-hAR through a prokaryotic or eukaryotic cell membrane. Other constructions may be used to join sequences encoding AFB1-hAR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and AFB1-hAR may be used to facilitate purification. One such expression vector provides for expression of a fusion protein containing AFB1-hAR and a nucleic acid encoding 6 histidine residues preceding a thioredoxin or an enterokinase cleavage site. The histidine residues facilitate purification on IMIAC (immnobilized metal ion affinity chromatography as described in Porath, J. et al. (1992, Prot. Exp. Purif. 3: 263–281) while the enterokinase cleavage site provides a means for purifying AFB1-hAR from the fusion protein. A discussion of vectors which contain fusion proteins is provided in Kroll, D. J. et al. (1993, DNA Cell Biol. 12:441–453).

In addition to recombinant production, fragments of AFB1-hAR may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of AFB1-hAR may be chemically synthesized separately and combined using chemical methods to produce the full length molecule.

THERAPEUTICS

Chemical and structural homology exists between AFB1-hAR and AFB1-AR from rat liver (GI 433611). In addition, AFB1-hAR is expressed in gastrointestinal and neoplastic disorders. Therefore, AFB1-hAR appears to play a role in the detoxification of AFB1 and related compounds and may reduce the toxicity and/or carcinogenicity of such compounds. AFB1-hAR is particularly useful for individuals at high risk for hepatoma, liver disease, or other disorders associated with AFB1 due to environmental or genetic factors.

Therefore, in one embodiment, AFB1-hAR or a fragment or derivative thereof may be administered to a subject to treat a gastrointestinal disorder. Such disorders include, but are not limited to, ascites, cholelithiasis, cholecystitis, cirrhosis, Crohn's disease, diverticulitis, fulminant hepatitis, gastritis, gastric and duodenal ulcers, hepatorenal syndrome, irritable bowel syndrome, jaundice, pancreatitis, and ulcerative colitis.

In another embodiment, a vector capable of expressing AFB1-hAR, or a fragment or a derivative thereof, may also be administered to a subject to treat a gastrointestinal disorder including, but not limited to, those described above.

In still another embodiment, an agonist which modulates the activity of AFB1-hAR may also be administered to a subject to treat a gastrointestinal disorder including, but not limited to, those described above.

In another embodiment, AFB1-hAR or a fragment or derivative thereof may be administered to a subject to treat a neoplastic disorder. Such disorders include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing AFB1-hAR, or a fragment or a derivative thereof, may also be administered to a subject to treat a neoplastic disorder including, but not limited to, those described above.

In still another embodiment, an agonist which modulates the activity of AFB1-hAR may also be administered to a subject to treat a neoplastic disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of AFB1-hAR may be produced using methods which are generally known in the art. In particular, purified AFB1-hAR may be used to produce antibodies or to screen libraries of pharmnaceutical agents to identify those which specifically bind AFB1-hAR.

Antibodies to AFB1-hAR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with AFB1-hAR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to AFB1-hAR have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of AFB1-hAR amino acids may be fused with those of another protein such as keyhole limpet hemocyanin and antibody produced against the chimeric molecule.

Monoclonal antibodies to AFB1-hAR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497;

Kozbor, D. et al. (1985) J. Immunol. Methods 81:31–42; Cote, R. J. et al. (1983) Proc. Natl.

Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce AFB1-hAR-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for AFB1-hAR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immnunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between AFB1-hAR and its specific antibody. A two-site, monoclonal-based immunoassay utilizing monoclonal antibodies reactive to two non-interfering AFB1-hAR epitopes is preferred, but a competitive binding assay may also be employed (Maddox, supra).

In another embodiment of the invention, the polynucleotides encoding AFB1-hAR, or any fragment or complement thereof, may be used for therapeutic purposes. In one aspect, the complement of the polynucleotide encoding AFB1-hAR may be used in situations in which it would be desirable to block the transcription of the mRNA. In particular, cells may be transformed with sequences complementary to polynucleotides encoding AFB1-hAR. Thus, complementary molecules or fragments may be used to modulate AFB1-hAR activity, or to achieve regulation of gene function. Such technology is now well known in the art, and sense or antisense oligonucleotides or larger fragments, can be designed from various locations along the coding or control regions of sequences encoding AFB1-hAR.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding AFB1-hAR. These techniques are described both in Sambrook et al. (supra) and in Ausubel et al. (supra).

Genes encoding AFB1-hAR can be turned off by transforming a cell or tissue with expression vectors which express high levels of a polynucleotide or fragment thereof which encodes AFB1-hAR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding AFB1-hAR (signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hamnmerhead motif ribozyme molecules that can specifically and efficiently catalyze endonucleolytic cleavage of sequences encoding AFB1-hAR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules.

These include techniques for chemically synthesizing oligonucleotides such as solid phase phosphoramidite chemical synthesis. Alternatively, RNA molecules may be generated by in vitro and in vivo transcription of DNA sequences encoding AFB1-hAR. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro. and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of AFB1-hAR, antibodies to AFB1-hAR, mimetics, agonists, antagonists, or inhibitors of AFB1-hAR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using a pharmaceutically acceptable carriers well known in the art in dosages suitable for oral administration. Such carriers enable the pharmnaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following:1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of AFB1-hAR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example AFB1-hAR or fragments thereof, antibodies of AFB1-hAR, agonists, antagonists or inhibitors of AFB1-hAR, which ameliorates the symptoms or condition. Therapeutic efficacy and toxicity may be determined by standard pharmnaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drag combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind AFB1-hAR may be used for the diagnosis of conditions or diseases characterized by expression of AFB1-hAR, or in assays to monitor patients being treated with AFB1-hAR, agonists, antagonists or inhibitors. antibodies useful for diagnostic purposes may be prepared in the same manner as those described above for therapeutics. Diagnostic assays for AFB1-hAR include methods which utilize the antibody and a label to detect AFB1-hAR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring AFB1-hAR are known in the art and provide a basis for diagnosing altered or abnormal levels of AFB1-hAR expression. Normal or standard values for AFB1-hAR expression are established by combining body fluids or cell extracts taken from normal mammalian subjects, preferably human, with antibody to AFB1-hAR under conditions suitable for complex formation The amount of standard complex formation may be quantified by various methods, but preferably by photometric, means. Quantities of AFB1-hAR expressed in control and disease samples, from biopsied tissues are compared with the standard values. Deviation between standard and subject values establishes the parameters for diagnosing disease.

In another embodiment of the invention, the polynucleotides encoding AFB1-hAR may be used for diagnostic purposes. The polynucleotides which may be used include oligonucleotide sequences, complementary RNA and DNA molecules, and PNAS. The polynucleotides may be used to detect and quantitate gene expression in biopsied tissues in which expression of AFB1-hAR may be correlated with disease. The diagnostic assay may be used to distinguish between absence, presence, and excess expression of AFB1-hAR, and to monitor regulation of AFB1-hAR levels during therapeutic intervention.

In one aspect, hybridization with PCR probes which are capable of detecting polynucleotide sequences, including genomic sequences, encoding AFB1-hAR or closely related molecules, may be used to identify nucleic acid sequences which encode AFB1-hAR. specificity of the probe, whether it is made from a highly specific region, e.g., 10 unique if nucleotides in the 5' regulatory region, or a less specific region, e.g., especially in the 3' coding region, and the stringency of the hybridization or amplification (maximal, high, intermediate, or low) will determine whether the probe identifies only naturally occurring to sequences encoding AFB1-hAR, alleles, or related sequences.

Probes may also be used for the detection of related sequences, and should preferably contain at least 50% of the nucleotides from any of the AFB1-hAR encoding sequences. The hybridization probes of the subject invention may be DNA or RNA and derived from the nucleotide sequence of SEQ ID NO:2 or from genomic sequence including promoter, enhancer elements, and introns of the naturally occurring AFB1-hAR.

Means for producing specific hybridization probes for DNAs encoding AFB1-hAR include the cloning of nucleic acid sequences encoding AFB1-hAR or AFB1-hAR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding AFB1-hAR may be used for the diagnosis of conditions or disorders which are associated with expression of AFB1-hAR. Examples of such conditions or disorders include gastrointestinal disorders such as ascites, cholelithiasis, cholecystitis, cirrhosis, Crohn's disease, diverticulitis, fulminant hepatitis, gastritis, gastric and duodenal ulcers, hepatorenal syndrome, irritable bowel syndrome, jaundice, pancreatitis, and ulcerative colitis, and neoplastic disorders such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding AFB1-hAR may be used in Southern or northern analysis, dot blot, or other membrane-based technologies; in PCR technologies; or in dipstick, pin, ELISA assays or microarrays utilizing fluids or tissues from patient biopsies to detect altered AFB1-hAR expression. Such qualitative or quantitative methods are well known in the art.

In a particular aspect, the nucleotide sequences encoding AFB1-hAR may be useful in assays that detect activation or induction of various cancers, particularly those mentioned above. The nucleotide sequences encoding AFB1-hAR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding AFB1-hAR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of AFB1-hAR, a normal or standard profile for expression is established. This may be accomplished by combining body fluids or cell extracts taken from normal subjects, either animal or human, with a sequence, or a fragment thereof, which encodes AFB1-hAR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the as disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding AFB1-hAR may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of AFB1-hAR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of non hybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode AFB1-hAR may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Venna et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding AFB1-hAR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, AFB1-hAR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between AFB1-hAR and the agent being tested, may be measured.

Another technique for drug screening which may be used provides for high throughput screening of compounds having suitable binding affinity to the protein of interest as described in published PCT application WO84/03564. In this method, as applied to AFB1-hAR large numbers of different small test compounds are synthesized on a solid substrate, such as plastic pins or some other surface. The test compounds are reacted with AFB1-hAR, or fragments thereof, and washed. Bound AFB1-hAR is then detected by methods well known in the art. Purified AFB1-hAR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding AFB1-hAR specifically compete with a test compound for binding AFB1-hAR. In this manner, the antibodies can be used to detect the presence of any peptide which shares one or more antigenic determinants with AFB1-hAR.

In additional embodiments, the nucleotide sequences which encode AFB1-hAR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAINOT14 cDNA Library Construction

The BRAINOT14 cDNA library was prepared from non-tumorous brain tissue removed from the left frontal lobe of a 40-year-old Caucasian female during excision of a cerebral meningeal lesion. Pathology for the associated tumor tissue indicated grade 4 gemistocytic astrocytoma. The patient presented with coma, epilepsy, incontinence of urine and stool, Type II-diabetes, and paralysis. Patient history included chronic nephritis. Patient medications included Decadron (dexamethasone) and phenytoin sodium.

The frozen tissue was homogenized and lysed using a Brinkmann POLYTRON homogenizer PT-3000 (Brinkmann Instruments, Westbury, N.J.) in guanidinium isothiocyanate solution. The lysate was centrifuged over a 5.7M CsCl cushion using an Beckman SW28 rotor in a Beckman L8–70M ultracentrifuge (Beckman Instruments) for 18 hours at 25,000 rpm at ambient temperature. The RNA was extracted with acid phenol pH 4.7, precipitated it using 0.3M sodium acetate and 2.5 volumes of ethanol, resuspended in RNAse-free water, and treated with DNase at 37° C. The RNA extraction and precipitation were repeated as before.

The mRNA was isolated with the OLIGOTEX kit (QIAGEN, Inc.; Chatsworth, Calif.) and used to construct the cDNA library. The mRNA was handled according to the recommended protocols in the SUPERSCRIPT plasmid system (Cat. #18248–013; Gibco/BRL). BRAINOT14 cDNAs were fractionated on a SEPHAROSE CL4B column (Cat. #275105–01; Pharmacia), and those cDNAs exceeding 400 bp were ligated into pINCY 1. The plasmid pINCY 1 was subsequently transformed into DH5 competent cells (Cat. #18258–012; Gibco/BRL).

II Isolation and Sequencing of cDNA Clones

Plasmid DNA was purified using the MINIPREP Kit (Catalogue #77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog #22711, GIBCO/BRL) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J Mol Biol 94:441f), using a Hamilton MICROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated and sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding AFB1-hAR occurs. Abundance and percent abundance are also reported. Abundance directly reflects the number of times a particular transcript is represented in a cDNA library, and percent abundance is abundance divided by the total number of sequences examined in the cDNA library.

V Extension of AFB1-hAR Encoding Polynucleotides

The nucleic acid sequence of the Incyte Clone 1596452 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amnplicons containing new, unknown nucleotide sequence for the region of interest. The initial primers were designed from the cDNA using OLIGO 4.06 Software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for12 cycles
Step 12 72° C. for 8 min
Step 13 4° C. (and holding)

A 5–10 $\mu$l aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA gel purification kit (QIAGEN Inc., Chatsworth, Calif.), and trimmed of overhangs using Klenow enzyme to facilitate religation and cloning.

After ethanol precipitation, the products were redissolved in 13 $\mu$l of ligation buffer, 1 $\mu$l T4-DNA ligase (15 units) and 1 $\mu$l T4 polynucleotide kinase were added, and the mixture was incubated at room temperature for 2–3 hours or overnight at 16° C. Competent E. coli cells (in 40 $\mu$l of appropriate media) were transformed with 3 $\mu$l of ligation mixture and cultured in 80 $\mu$l of SOC medium (Sambrook et al., supra). After incubation for one hour at 37° C., the E. coli mixture was plated on Luria Bertani (LB)-agar (Sambrook et al., supra) a containing 2× Carb. The following day, several colonies were randomly picked from each plate and cultured in 150 $\mu$l of liquid LB/2× Carb medium placed in an individual well of an appropriate, commercially-available, sterile 96-well microliter plate. The following day, 5 $\mu$l of each overnight culture was transferred into a non-sterile 96-well plate and after dilution 1:10 with water, 5 $\mu$l of each sample was transferred into a PCR array.

For PCR amplification, 18 $\mu$l of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 Software (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS membrane, Schleicher & Schuell, Durham, N.H.). Hybridization is cared out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots or the blots are placed in a PHOSPHOIMAGER cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the AFB1-hAR-encoding sequence, or any part thereof, is used to decrease or inhibit expression of naturally occurring AFB1-hAR. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of AFB1-hAR, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the AFB1-hAR-encoding transcript.

IX Expression of AFB1-hAR

Expression of AFB1-hAR is accomplished by subcloning the cDNAs into appropriate vectors and transforming the vectors into host cells. In this case, the cloning vector is also used to express AFB1-hAR in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of AFB1-hAR into the bacteria growth media which can be used directly in the following assay for activity.

X Demonstration of AFB1-hAR Activity

The reductase activity of AFB1-hAR towards 4-nitrobenzaldehyde is assayed spectrophotometrically as described by Hayes, et al. (supra). Activity of AFB1-hAR towards AFB1 is measured by the HPLC-based assay described by Judah, et al. (supra).

XI Production of AFB1-hAR Specific Antibodies

AFB1-hAR that is substantially purified using PAGE electrophoresis (Sarnbrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems peptide synthesizer model 431 A using fmoc-chemistry, and coupled to keyhole limpet hemocyanin (KLH, Sigmna, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring AFB1-hAR Using Specific Antibodies

Naturally occurring or recombinant AFB1-hAR is substantially purified by immunoaffinity chromatography using antibodies specific for AFB1-hAR. An immunoaffinity column is constructed by covalently coupling AFB1-hAR antibody to an activated chromatographic resin, such as CNBr-activated SEPHAROSE (Pharmnacia & Upjohn). After the coupling, the resin is blocked and washed according to the manufacturer's instructions.

Media containing AFB1-hAR is passed over the immunoaffinity column, and the column is washed under conditions that allow the preferential absorbance of AFB1-hAR (e.g., high ionic strength buffers in the presence of detergent). The column is eluted under conditions that disrupt antibody/AFB1-hAR binding (eg, a buffer of pH 2–3 or a high concentration of a chaotrope, such as urea or thiocyanate ion), and AFB1-hAR is collected.

XIII Identification of Molecules Which Interact with AFB1-hAR

AFB1-hAR or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled AFB1-hAR, washed and any wells with labeled AFB1-hAR complex are assayed. Data obtained using different concentrations of AFB1-hAR are used to calculate values for the number, affinity, and association of AFB1-hAR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

I claim:

1. An isolated and purified polynucleotide encoding a polypeptide comprising the amino acid sequence of SEQ ID NO:1.

2. A composition comprising the polynucleotide of claim 1.

3. An isolated and purified polynucleotide which is completely complementary to the polynucleotide of claim 1.

4. An isolated and purified polynucleotide comprising SEQ ID NO:2.

5. An isolated and purified polynucleotide which is completely complementary to the polynucleotide of claim 4.

6. An expression vector comprising the polynucleotide of claim 1.

7. A host cell comprising the expression vector of claim 6.

8. A method for producing a polypeptide comprising the amino acid sequence of SEQ ID NO:1, the method comprising the steps of:
   a) culturing the host cell of claim 7 under conditions suitable for the expression of the polypeptide; and
   b) recovering the polypeptide from the host cell culture.

* * * * *